United States Patent
Rahum

(10) Patent No.: US 9,782,078 B2
(45) Date of Patent: Oct. 10, 2017

(54) DEVICE, SYSTEM AND METHOD FOR BLOOD VESSEL IMAGING AND MARKING

(71) Applicant: Uzi Rahum, Be'er Sheva (IL)

(72) Inventor: Uzi Rahum, Be'er Sheva (IL)

( * ) Notice: Subject to any disclaimer, the term of this patent is extended or adjusted under 35 U.S.C. 154(b) by 575 days.

(21) Appl. No.: 14/179,796

(22) Filed: Feb. 13, 2014

(65) Prior Publication Data

US 2014/0236019 A1 Aug. 21, 2014

Related U.S. Application Data

(63) Continuation-in-part of application No. PCT/IL2012/050303, filed on Aug. 12, 2012.

(60) Provisional application No. 61/764,283, filed on Feb. 13, 2013, provisional application No. 61/523,369, filed on Aug. 14, 2011.

(51) Int. Cl.
*A61B 5/00* (2006.01)

(52) U.S. Cl.
CPC .................................. *A61B 5/0075* (2013.01)

(58) Field of Classification Search
None
See application file for complete search history.

(56) References Cited

U.S. PATENT DOCUMENTS

| | | | | |
|---|---|---|---|---|
| 5,407,440 A | * | 4/1995 | Zinreich | A61B 19/54 600/436 |
| 6,464,646 B1 | * | 10/2002 | Shalom | A61B 5/01 600/481 |
| 7,288,578 B2 | * | 10/2007 | Phelan | C09D 11/101 522/84 |
| 2007/0161909 A1 | * | 7/2007 | Goldman | A61B 5/0059 600/476 |
| 2008/0287806 A1 | * | 11/2008 | Wood | A61B 5/0059 600/473 |
| 2009/0163809 A1 | * | 6/2009 | Kane | A61B 19/52 600/443 |
| 2011/0310381 A1 | * | 12/2011 | Kamata | G01J 1/44 356/218 |
| 2012/0029417 A1 | * | 2/2012 | Samain | A61K 8/49 604/20 |

* cited by examiner

*Primary Examiner* — Joseph M Santos Rodriguez

(57) ABSTRACT

The present invention relates to a system and a method for blood vessel imaging, detection, and marking and in particular, to such a system and method in which optical enhancers are utilized to increase the accuracy and quality of the process for detecting a blood vessel.

20 Claims, 9 Drawing Sheets

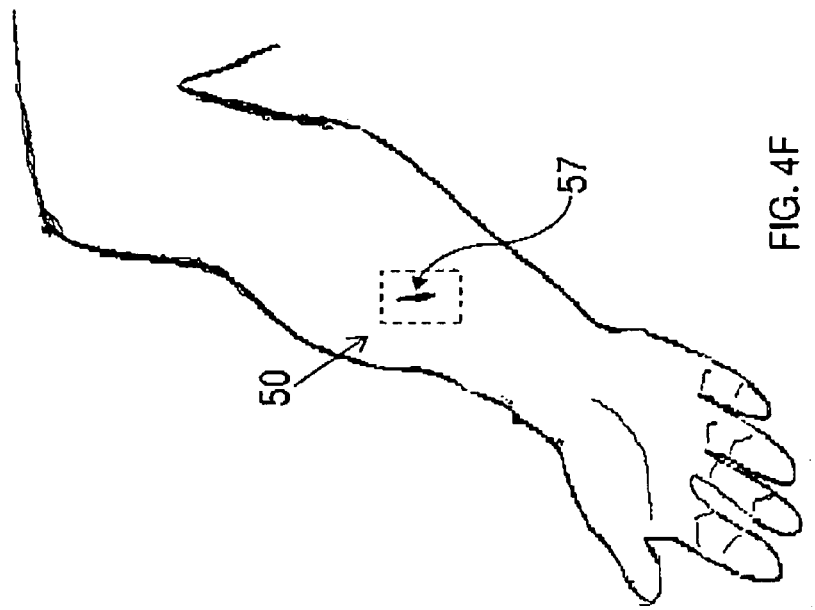
FIG. 4F
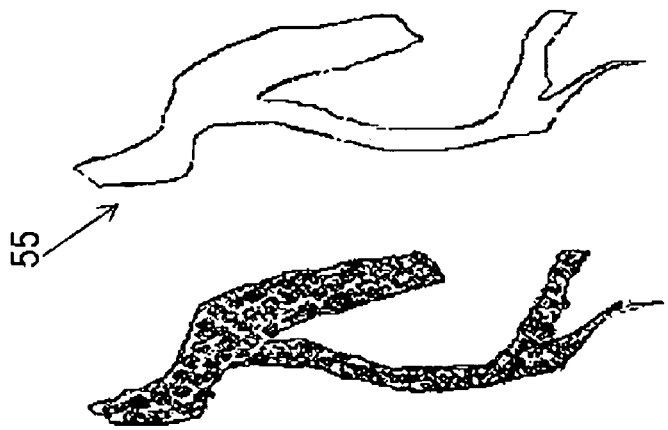
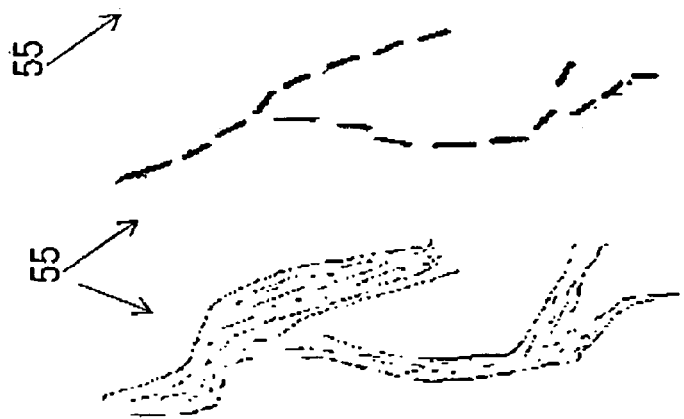

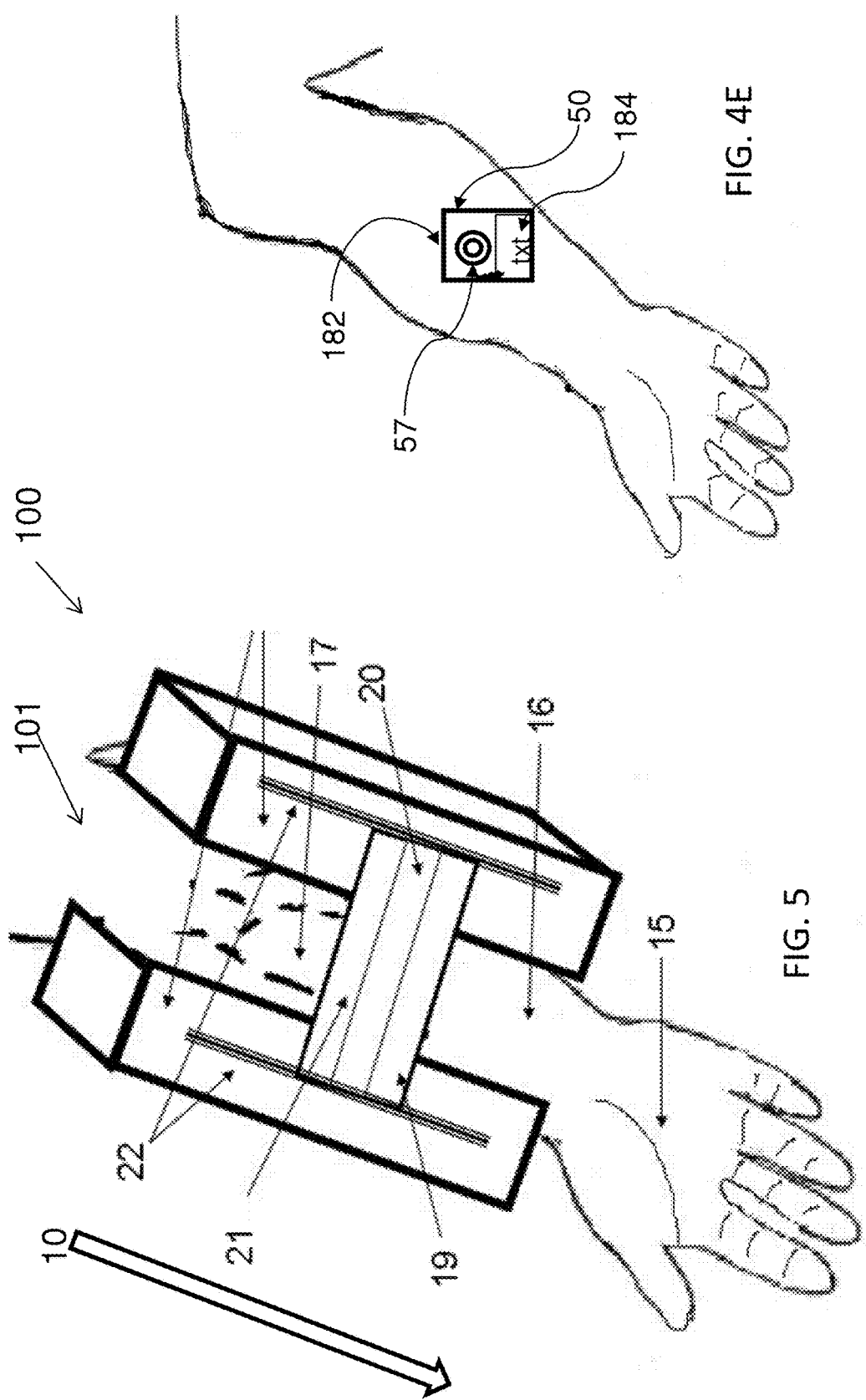

DEVICE, SYSTEM AND METHOD FOR BLOOD VESSEL IMAGING AND MARKING

RELATED APPLICATIONS

This application is a Continuation in Part of, and claims priority from, PCT Application No. PCT/IL2012/050303, filed on Aug. 12, 2012, which claims priority from U.S. Provisional Application No. 61/523,369, filed on Aug. 14, 2011, and also claims priority from U.S. Provisional Application No. 61/764,283, filed on Feb. 13, 2013, all of which are hereby incorporated by reference in its entirety.

FIELD OF THE INVENTION

The present invention relates to a device, system and a method for blood vessel imaging, detection, and marking and in particular, to such a device, system and method in which optical enhancers are utilized to increase the accuracy and quality of the process for detecting a blood vessel.

BACKGROUND OF THE INVENTION

Access to the blood stream via a needle is perhaps the most common procedure administered by healthcare professionals, and may be referred to as Blood Vessel Medical Treatment (hereinafter referred to as 'BVMT'). Access to the blood stream is required both for the administration of drugs, for example intravenous drug administration via a drip, and/or for monitoring purposes, via blood testing for example for tracking an analyst such as glucose levels, cholesterol, cardiac enzymes and the like. Therefore access to the blood stream is requirement for most medical testing and monitoring procedures. However to date, despite technological advancements identification and gaining access to the blood stream remains a difficult procedure for some groups, particularly for the young, old, premature babies and obese individuals. This is due to the fact that visualization of the blood vessel is not readily available to the naked eye while practitioners rely on experience and skill to quickly and properly identify the blood vessel so as to gain access to it.

The lack of visibility in these groups may be due to various reasons: location (depth of vessel), size (small thickness). Difficulty in locating the vessels makes the needle intrusion procedure very difficult and at times risky, resulting in many false attempts leading to multiple and needless needle penetrations.

Technology currently available to facilitate blood vessel identification have been introduced to attempt to identify the location of a blood vessel by non-invasive visual means using heat, ultrasound, and light sources. However these systems are limited in a variety of ways, for example they are cumbersome, expensive to manufacture, difficult to use, and at times do not accurately identify the blood vessel location.

Currently there are number of available products for locating BVs. This include products utilizing (1) Ultrasonic imaging, such as the Bard Site-Ride 5 Ultrasound system marketed by Bard Access Systems, INC. of Salt Lake City, Utah, (2) NIR Imaging, such as the IRIS Vascular Viewer marketed by Infrared Imaging Systems, INC and the Vein-Viewer Imaging systems marketed by Cristis (Luminetx), (3) Liquid Crystal thermal surface temperature measurement patches, such as the K-4000 Vena-Vue Thermographic Vein Evaluator manufactured by Biosynergy, Inc. of Elk Grove Village, Ill., (4) visible light illumination, such as the Venoscope II Transilluminator/Vein Finder and the Neonatal Transilluminator marketed by Venoscope, L.L.C. of Lafayette, La., and the VeinLite LED, Veilite EMS and Veinlite PEDI manufactured by TransLite LLC of Sugar Land, Tex.

The infrared ('IR') and/or near infrared ('NIR') imaging techniques relies on the fact that blood vessels have low light reflection in the IR wavelength spectrum. At this wavelength range, the difference in reflection between blood vessel and skin is very high. Thus an IR imaging system can obtain much better indication of the blood vessel location particularly when compared to the naked eye.

Systems utilizing IR/NIR for blood vessel location are known by the name of Vein-Viewers that project the capture image back on the body surface, thus enabling the operator to easily locate the blood vessel. Such systems are commercially available and they become more and more distributed in the world. It was proven that those tools dramatically improve the rate success of blood vessel intrusion. It is the intention of the presented method to simplifying those methods while reducing the cost and improving efficiency while keeping the system performance. An example of such a system is described in U.S. Pat. Nos. 5,969,754 and 6,556,858 incorporated herein by reference as well as a publication entitled "The Clinical Evaluation of Vein Contrast Enhancement".

Luminetx is currently marketing such a device under the name "Veinviewer Imaging System" and information related thereto is available on its website, which is incorporated herein by reference.

The Luminetx Vein Contrast Enhancer (hereinafter referred to as 'LVCE') utilizes an infrared light source for flooding the region to be enhanced with infrared light generated by an array of LEDs. A CCD imager is then used to capture an image of the infrared light reflected off the patient. The resulting captured image is then projected by a visible light projector onto the patient in a position closely aligned with the image capture system. Given that the CCD imager and the image projector are both two dimensional, and do not occupy the same point in space, it is relatively difficult to design and build a system that closely aligns the captured image and the projected image.

A further characteristic of the LVCE is that both the imaging CCD and the projector have fixed focal lengths. Accordingly, the patient must be at a relatively fixed distance relative to the LVCE. This necessitates that the LVCE be positioned at a fixed distance from the region of the patient to be enhanced.

The LVCE system, for example by luminetx is limited in that it required that the system be mobile to reach individual patients and therefore limited in its use in that they system has to be used in real time to provide its effect however its use remains in a one to one ratio where each system requires a system, practitioner and patient in real time in order to utilize the system.

Other systems have attempted to overcome this problem by introducing a miniature mobile vein enhancer, described in U.S. Pat. No. 7,904,138 to Goldman et al, where the enhancer may be worn by a patient during the procedure. However this does not overcome the problem of needing a one to one to one ratio, where patient, device and practitioner have to be on site in real time to realize the device's potential as it projects an enhanced image of the scanned area onto the target site.

Other systems such as that described by U.S. Pat. No. 6,464,646 to Shalom et al, teach a temperature sensitive device capable of locating and marking a hot spot about a treatment area of scanned skin. However such a system is limited in that a temperature based system is dependent on temperature changes, which is highly variable and cannot produce sufficiently repetitive and accurate depiction of the location of a blood vessel. Accordingly although a hot spot may be identified and potentially marked, the hot spot location cannot guarantee the location of a blood vessel over time, due to temperature fluctuations over time.

SUMMARY OF THE INVENTION

It is important to notice that in current vein viewing systems, a real time image is required to allow a practitioner to find the blood vessel. Accordingly the vein viewing device and/or system must be utilized in real time, that is during the blood extraction process. Accordingly, the current vein viewing system are limited in that they do not provide for en-mass use, rather a single system must be used per each extraction process, therein greatly limiting the efficiency of the device. Accordingly, the system throughput and/or efficiency remain equivalent to a user's ability to extract blood.

This limitation influences the cost effectiveness of the system and its return of investment form economical view point. It is clear that cost reduction of such vein viewing system and throughput increase of such system will increase its cost effectiveness and its use in medical institutes will increase.

A blood vessel enhancing device and/or system that provides better and/or more efficient blood vessel identification particularly for en-mass applications is warranted and is not provided by the state of the art devices.

The present invention overcomes the deficiencies of the background by providing a system and method for identifying and blood vessel location in a non-invasive manner in such a way as to allow accurate identification of the blood vessel that may be repeatable while allowing offline access to the identified blood vessel. Particularly the present invention overcomes the prior art by providing a system and method for accurately identifying the blood vessel location by way of non-invasive imaging of a target area and printing the non-invasive onto the scanned area or onto a substrate associated with the scanned area. Therefore embodiments of the present invention provide for offline viewing and access to a blood vessel. In this manner, the one (device) to one (patient) to one (practitioner) ratio, as provided by the prior art, is no longer necessary, as an image of the target area is captured and outputted. In this way a practitioner may perform the procedure at any point in time and is not dependent on immediate availability of the imaging device. Accordingly, blood vessel identification may be performed at different time from that of the needle puncture procedure, and therefore allows for "offline" use.

Most preferably the system according to the present invention provides a single system to be used for many patients and many practitioners, therein alleviating the need for a one system to one patient to one practitioner ratio, where the use of the blood vessel system enhancer is limited to online, single bedside use, as provided by the prior art.

Instead the blood vessel enhancing system, according to the present invention, may be used for many patients, first to identify and print the blood vessel location, and thereafter preforming the needle access as necessary. Therefore a one device to one patient ratio and thereafter as necessary a one patient to one practitioner ratio is required. Such that the process of blood vessel access by way of a needle access may be streamlined and may be provided for many patients by a single practitioner.

Within the context of this application the term blood vessel ('BV') may interchangeable be referred to any vessel, artery, vein, carrying blood.

Within the context of this application the term Blood Vessel Medical Treatment may be interchangeably referred to as 'BVMT'.

An optional embodiment of the present invention provides a method for blood vessel recognition is provided by applying or projecting light onto the object of interest, such as a patient arm or leg. The diffused light from the object of interest, which has different optical properties such as: polarization, absorption, reflection and/or scattering for blood vessel and skin, is then collected by optical sensor and the data is processed to distinguish the blood vessels from surroundings tissue such as skin, hair, scars, freckles, beauty spots, moles and other permanent marks on the skin (hereinafter referred to as 'V-noise').

In one embodiment of the present invention the system may comprise a light source producing light in the infrared ('IR') range that illuminates the inspected body part which is needed for BVMT. The light source can be any kind of source that has different absorption/reflection light properties when it interacts with skin and blood vessel. Light source with high polarization ratio enables better contrast for identifying blood vessels than light with low polarization ratio.

The diffused light from the object is collected by optical sensor(s). The Light Signal Collector (hereinafter referred to as 'LSC') may be provided in the form of a camera module; CCD, CMOS, line CCD, photo-detector or any type of detector that can collect the scattered light from the object. The IR LSC is positioned besides the light source and receives the reflected light. An IR band pass filter may be positioned in front of the LSC, to restrict the collected light to the same wavelength of the light source. The use of the IR filter and/or polarizer enhances the captured signal quality since it rejects non useful reflected light. The captured signal may be processed by a computer in means of image filtering and enhancement.

Optionally and preferably the system according to the preset invention provides for minimal alignment error between the projected image and the captured image. Most preferably the error is less than about 0.25 mm.

Optionally an image processing techniques, optionally provided by the system processor, may compensate for alignment requirement between the camera and the projector. Optionally such image processing techniques may compensate for the relative alignment errors between the image capturing and image projection.

Optionally a processor may provide for converting and/or compensating for image resolution difference between image capturing device and image projection device. For example image capture may be provided in VGA resolution 640×480 pixels, while image projector may be QVGA having a resolution of 320×240 pixels.

Optionally a preliminary alignment and/or calibration process between image capturing module and projecting apparatus may be required.

Additional miss-alignment errors may, for example, be caused by the different angle of sight between the receiving camera and the image projector. Since there is an angle between the camera and projector it generates a miss-alignment error that depends on the body object distance to the device. Thus the design of such system should minimize this angle.

In one embodiment of the present invention blood vessel system station may be used for multiple BVMT operations done by multiple medical staff in parallel and/or simultaneously.

For instance such vein visualization and marking station may be used as part of the preparation procedure of the patient for such BVMT at relatively short time.

Then, the patient goes to one or more medical staff that uses the marks to easily find the required blood vessel and apply said BVMT. The need for the real time diagnostic is eliminated.

Unless otherwise defined the various embodiments of the present invention may be provided to an end user in a plurality of formats, platforms, and may be outputted to at least one of a computer readable memory, a computer display device, a printout, a computer on a network or a user.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof.

Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Although the present invention is described with regard to a "computer" on a "computer network", it should be noted that optionally any device featuring a data processor and/or the ability to execute one or more instructions may be described as a computer, including but not limited to a PC (personal computer), a server, a minicomputer, a cellular telephone, a smart phone, a PDA (personal data assistant), a pager, or the like. Any two or more of such devices in communication with each other, and/or any computer in communication with any other computer, may optionally comprise a "computer network".

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 3A showing a perspective view of the enhancer system; FIG. 3B showing schematic a top view of the enhancer system;

FIG. 4A-D show optional depictions of the output printout of the system according to optional embodiments of the present invention;

FIG. 4E-F is an illustrative depiction of an optional output of the system according to an optional embodiment of the present revealing an optimal position and/or location for needle insertion;

FIG. 5 shows a schematic illustration of an optional embodiment of the present invention, showing an optional stationary system according to an optional embodiment of the present invention;

DESCRIPTION OF THE PREFERRED EMBODIMENTS

The principles and operation of the present invention may be better understood with reference to the drawings and the accompanying description.

The following figure reference labels are used throughout the description to refer to similarly functioning components are used throughout the specification hereinbelow.

10 target area scanning direction;
15 forearm target area;
16 un-scanned portion of target area;
18 housing;
22 rail
26 rail track system
27 auxiliary fixation device;
50 target area;
20,52 scanning site/imaging line;
54 printing site;
17, 55 detected blood vessel;
57 detected optimal position;
103 scanning distance;
100, 200 blood vessel enhancing imaging system;
101 enhancer housing;
105 scanner/image capture module;
19, 110 illumination unit;
112 illumination source and/or generator
19,114 illumination head;
116 incident light;
120 detector unit;
122 reflected light;
124 optics member;
126 light sensor;
130 processing module;
132 processor;
135 display module;
140 output module (printer);
142 output cartridge;
21,144 output head;
150 optical enhancer;
160 auxiliary device;
180 medium,
182 sticker;
184 text area.

Figure 1:
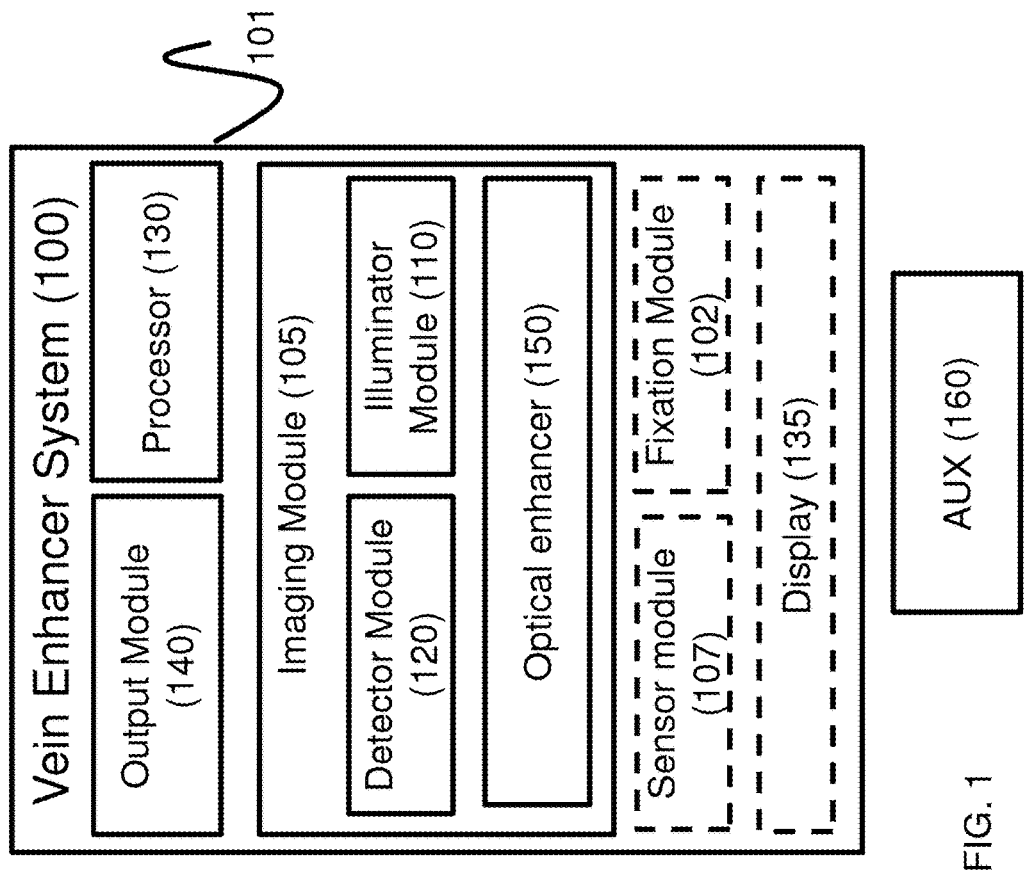
FIG. 1 is a schematic block diagram of an exemplary system according to optional embodiments of the present invention.

Referring now to the drawings, FIG. 1 is a schematic block diagram of an exemplary system 100 according to the present invention for a blood vessel enhancing and printing system. Most preferably system 100 provides for non-invasively identify blood vessel 55 underlying a target area 50 for example on an extremity such an arm, hand, leg or the like. Most preferably system 100 comprises a housing 101, output module 140, processing module 130 an imaging module 105. Optionally and preferably system 100 may further comprise a display 135 provided to display the enhanced blood vessel image and/or as a user interface.

Most preferably housing 101 provides for receiving and/or associating with the target area 50 to be scanned. For example, housing 101 may be provided in the form of an elongated tube to facilitate receiving an extremity, for example an arm, hand or the like portion of the body to be scanned.

Optionally housing 101 may further comprise a localization and/or fixation module 102 provided to ensure the targeted area is securely coupled with system 100 and for preventing movement of the target area while imaging and enhancement is performed. Optionally fixation module 102 may be provided in the form of an elongated sleeve housing adapted to receive an extremity for example an arm. Optionally and preferably fixation module 102 may comprising an inflatable cuff provided to facilitates securing the target area within fixation module 102 housing and to ensure that scanning is performed relative to a reference point.

Optionally housing 101 may further comprise an optional sensor module 107 comprising at least one or more sensors that may facilitate the enhancement process and/or to provide further detail regarding the user. Optionally sensor module 107 may for example include but is not limited to at least one or more sensors selected from the temperature sensor, pressure sensor, illumination sensor, background light sensor, blood pressure sensor, heart rate sensor, the like or any combination thereof.

Optionally and preferably system 100 and housing 101 may be disposed in a central location, for example a nurses station, where a plurality of patients (users) may sequentially (in turn) use system 100 to identify an optimal location 57 for accessing the blood vessel within a scanned target area 50. For example a plurality of patients in line for blood test may sequentially use system 100 to scan their arm to identify their individual optimal location 57 for the blood test and to mark the optimal position 57 by way of a printout either directly over the location on the target area or over a substrate 180 such as a sticker 182. Most preferably, such an arrangement provides for en-mass utilization of the system 100. Most preferably imaging module 105 provides for obtaining an image of a target area 50, wherein based on the obtained image, the processing unit 130 provides for enhancing and processing the image to identify and reveal a blood vessel 55 underlying the target area 50.

Most preferably once the image of the target area is enhanced and an image of an identified blood vessel 55 is available the image may be outputted with output module 140.

Most preferably output module 140 may be provided in the form of a printer and/or printer head that may optionally print an enhanced blood vessel image directly on the target area 50, or about a medium 180 and/or substrate 180, for example a sticker 182, that may be coupled over target area 50.

Most preferably the target area may be an area of skin overlying blood vessel for example about the forearm, arm, hand, palm, leg or any anatomical area of a human or animal. Optionally and preferably an image of identified blood vessel 55 within the targeted area 50 may be printed directly on the skin surface above the anatomical location of the blood vessel.

Optionally and more preferably output module 140 may print the enhanced blood vessel image and/or outputted image 55 about a substrate, that may optionally and preferably be associated over target area 50. A substrate 180 that may for example include but is not limited to a sticker, associated with target area 50 and interfacing system 100. Optionally substrate 180 may for example be a spray and/or fluid and/or foam and/or film or the like material that may be applied over target area 50 and that may be allowed to gel and/or harden prior to printing an image of the detected enhanced blood vessel 55.

Figure 8:
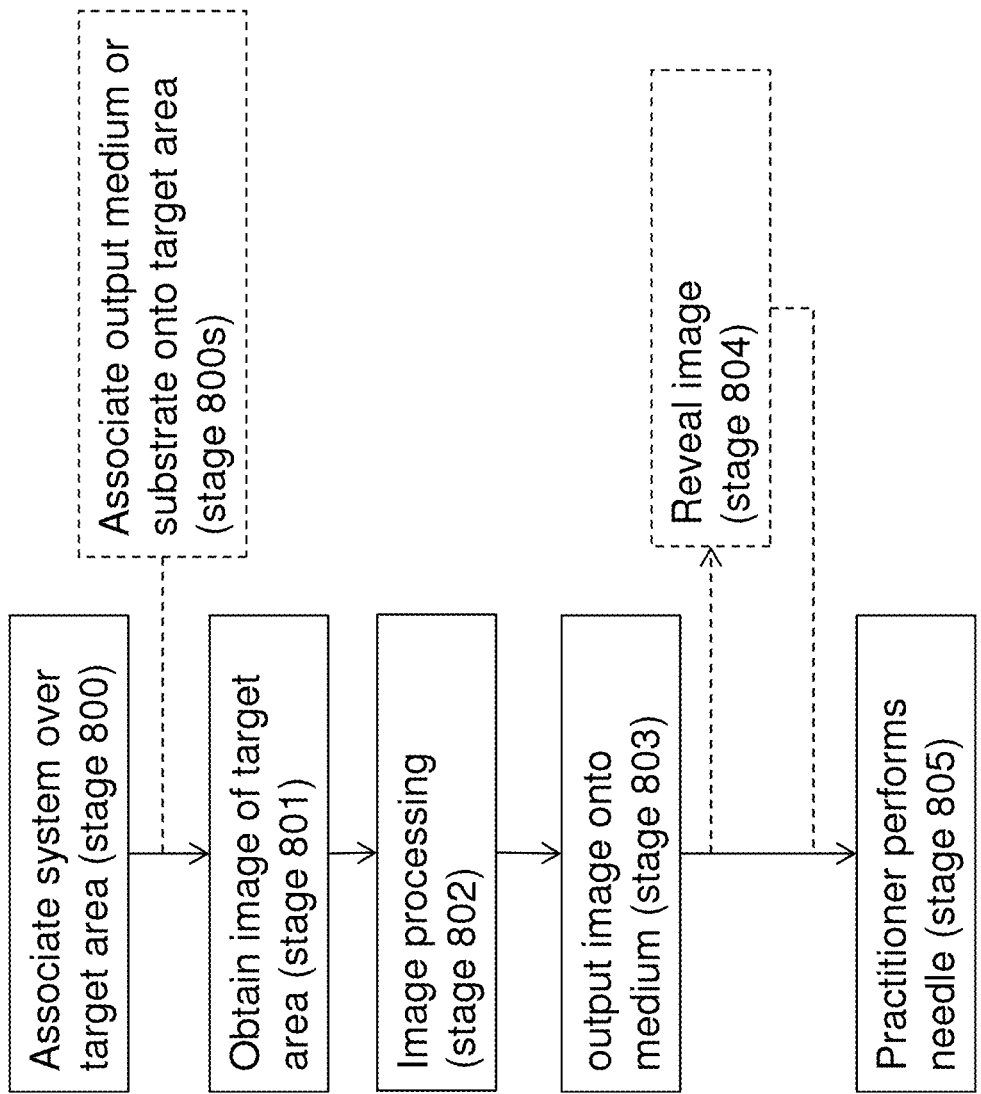
FIG. 8 shows a flowchart of an optional method according to the present invention.

Optionally output module 140 may provide for marking an optimal location 57 for needle penetration along a detected blood vessel 55 and within a target area 50, FIG. 4F. Optionally module 140 may provide for marking optimal location 57 by placement of a sticker or the like medium and/or substrate 180 to indicate to a practitioner the optimal needle access point within target area 50. Optionally optimal location 57 sticker may be provided in a plurality of optional shapes, more preferably each shape may comprise an opening and/or recess and/or window indicative of the location for the optimal needle access point. For example, an optimal location sticker may be provided in the form of a donut shaped sticker, where the opening is indicative of the optimal needle access point within target area 50, for example as shown in FIG. 8.

Optionally and most preferably processing module 130 may further provide for identifying and/or locating an optimal needle access point 57 along a detected blood vessel 55 within target area 50. Optionally processing module may identify a plurality of optimal points 57, and allow a user, for example a medical practitioner and/or nurse, to select at least one.

Optionally processing module 130 may further provide for determining and/or estimating at least one or more needle parameters associated at various points along detected blood vessel 55 and particular about at least one or more optimal penetration point 57. Optionally processing module 130 may provide for determining needle parameters for example including but not limited to needle gage, depth of penetration, angle of penetration, needle size, needle length, the like or any combination thereof.

Optionally processing module 130 may be utilized to determine the depth of penetration over a particular location may be determining and/or estimated by assuming the blood vessel is a rounded pipe and therefore the dimension of the detected blood vessel may be determined.

Optionally the needle parameters determined with processing module 130 may be further utilized to determine at least one or more outputting and/or printing function of output module 140. For example, the output module 140 may print messages and/or color coded stickers in order to convey the needle parameters determined with module 130. For example output module may include textual instructions relating to the needle gage, penetration angle, over an area 184 of a sticker 182 and/or medium 180 for example as shown in FIG. 4E. Optionally color coding may be outputted to a medium 180 and/or a sticker 182 and/or substrate 180 to convey at least one or more optional needle parameters. For example, a green colored sticker and/or medium produced by module 140 may be indicative of the needle gage to be used.

Most preferably processor module 130 may be realized in the form of a microprocessor, circuitry, hardware and/or software that facilitates the operation of and/or control system 100. Most preferably processor module 130 provides for image processor techniques that facilitate the identification of blood vessel 55 based on the illumination source and the detected image provided by imaging module 105 and interaction with target area 50. Optionally and most preferably processing module 130 may further provide for identifying and/or locating an optimal needle access point 57 along a detected blood vessel 55 within target area 50.

Most preferably imaging module 105 comprises an illumination module 110 and detector module 120. Most preferably imaging module further comprises at least one or more optical enhancers 150 provided to facilitate the identification of a blood vessel within target area 50.

Most preferably illumination module 110 is provided for generating a light source to illuminate a target area 50, therein providing an incident light source for system 100.

Optionally illumination source 110 may comprise at least one or more light sources. Optionally the light source may have a wavelength from about 455 nm up to about 940.

Optionally a plurality of illumination sources may be utilized with system 100. Optionally at least one or more light sources may be utilized in the wavelength in the range from about 650 nm up to about 1000 nm.

Optionally illumination module 110 may provide for a light source and/or illumination source, optionally the angle at which the light source is projected may be controllable. Optionally the light source projection angle is controllable relative to the target area. Optionally a plurality of light sources may be provided with different projection angles. Optionally the illumination source projection angle may be controllably changed while imaging a target area.

Optionally control of the projection angle may be controlled with controller module 130.

Optionally the different illumination projection angles and/or wavelengths, may be utilized for enhancing the image of target area 50. Optionally and preferably illumination projection angles and/or wavelengths provide for enhancing image of target area 50 for identifying a detected blood vessel 55 by way of providing a multi-layer image.

Most preferably detector module 120 provides for detecting the reflection of incident light after its interaction with target area 50. Most preferably detector module 120 comprises at least one or more image and/or light sensors that are provide for converting the reflected light into an image.

Optionally and preferably a light sensitive sensors and/or light detectors comprising detector module 120 may for example include at least one more but is not limited to at least one or more of: photodetectors, camera, CCD, line CCD, CMOS, the like light detector, any combination thereof.

Optionally and preferably detector module 120 may comprise two or more light detectors and/or a plurality of light detectors that work in a coordinated manner relative to one another to obtain an improved image of target area 50. Optionally each light detector forming module 120 may function in a coordinated manner, optionally each light detector comprising module 120 may provide an image that may optionally be superimposed over other generated images. Optionally a plurality of light detectors may provide a plurality images that may be processed by processing module 130, optionally providing a plurality images that may be layered and/or superimposed to further provide an improved and or enhanced image where the signal to noise ratio ('SNR') is improved therein further enhancing the image of a target area.

Most preferably imaging module 105 comprises optical enhancers module 150, optionally comprising at least one and more preferably a plurality of optical enhancers. Optionally optical enhancers may be associated with at least one or both of illuminating module 110 and/or detector module 120. Optionally optical enhancers 150 may for example be realized in the form of filters, polarizer, wave plate, the like or any combination thereof to facilitate controlling the properties of the illumination source emanating from module 110 and/or the reflected light toward detector module 120.

Most preferably enhancers 150 provide for enhancing the image by controlling the polarization properties of at least one of or both of the illuminating light and/or reflected light.

Optionally and preferably optic enhancers 150 utilized according to the present invention includes liquid crystal cell ('LCC') for example including but not limited to pi-cell liquid crystal, Twisted Nematic ('TN') liquid crystal cell, liquid crystal polarization rotator, liquid crystal polarization retarder, the like or any combination thereof.

Most preferably a Liquid Crystal Cell (LCC) is an electro-optics element that provides for rotating the polarization and/or filtering polarization and/or controlling the polarization orientation, provided to control at least one or both of the incident illuminating source emanating from module 110 and/or the detected light with detector module 120.

Most preferably the optical properties of a blood vessel, for example reflectivity and/or absorption, may be sensitive to polarization orientation of the wavelengths utilized to obtain the blood vessel image. Most preferably utilizing a plurality of images obtained with the system 100 utilizing an LCC enhancer to change the wavelength's polarization orientation provides for improved images of a target area, and in particular allows to superimpose a number of combination to improves blood vessel enhancement.

Most preferably a plurality of optic enhancers 150 provided in the form of an LCC may be controlled relative to one another. Most preferably such control provides for obtaining a multi-layered perspective of the imaged target area 50, therein immensely improving the processing ability provided by processor module 130. Most preferably control of the LCC polarization may be provided with controller module 130. Most preferably an enhancer 150 in the form of LCC provides the freedom to use a plurality of a various polarization angles that may be evaluated relative to one another. Most preferably utilizing optic enhancer in the form of LCC provide an enhanced image of the target area 50, therein providing for a plurality of optional layers and processing options, for example including but not limited to superimposing a plurality of images having different optic properties (polarity rotation), to obtain an enhanced image of target area 50.

Optionally an LCC enhancer may provide for rotating the polarity by any controllable degree up to about 180 degrees, more preferably up to about 90 degrees.

Most preferably enhancer 150 in the form of a liquid crystal cell provides for rotating the polarity of light, where most preferably the degree of the rotation may be controlled with a control signal from a processor and/or controller module 130. For example a control signal may be provided in the form of an electrical current. Optionally control of and LCC enhancers 150 provides for controlling the degree of polarity rotation of the LCC may be provided with respect to a plurality of optional parameters and/or system members, for example including but not limited to, the target area 50, image processing techniques utilized, type of illumination source, illumination unit 110, other optical enhancers utilized 114, type of detector, detector module 120, ambient environmental factors, any combination thereof or the like.

Optionally system 100 may interface with a plurality of optional auxiliary devices 160 about any member of system 100. Optionally an auxiliary device 160 may interface with housing 101, for example to facilitate mobilizing system 100 about target area 50, for example as described in FIG. 5-6.

Optionally system 100 may interface with an auxiliary device 160 provided in the form of a computer and/or processor and/or smartphone or the like about processing module 130. For example processing module 130 may interface with an auxiliary device 160 comprising a processor to facilitate processing a detected image. Optionally auxiliary device 160 may be utilized to interface with processing module 130 to store data or the like.

An optionally auxiliary device 160 may optionally interface with output module 140 for example to facilitate printing and/or marking of a blood vessel. Optionally auxiliary device 160 may provide a substrate 180 and/or medium about which the outputted image may be printed. Optionally, auxiliary device 160 may be provided in the form of a cartridge comprising a spacer and/or substrate 180 and/or medium for output module 140.

Optionally auxiliary device 160 may be provided in the form of a personalized single use sticker 182 and/or printing substrate 182 and/or medium 180 or the like or any combination thereof that may be associated with a user over a target area.

Optionally housing 101 may be realized and/or configured in a plurality of optional forms for example as a hand held mobile device (FIG. 7), a stationary device with functionally moving part (FIG. 5), a stationary device, a mobile device or the like. Optionally housing 101 may interface with optional devices to facilitate operation of system 100, for example as described in FIG. 5-6.

Optionally display 135 may be provided in the form of a screen and/or an interactive touch screen capable of displaying to a user an image of the enhanced blood vessel image as produced with processing module 130. Optionally the enhanced image of a detected blood vessel 55 may be displayed to a user on display 135 prior to rendering the image to output module 140. Optionally a displayed enhanced image 55 may further display to a user the identified optima location 57. Optionally a user, for example a medical practitioner and/or nurse, may be allowed to alter the location of the optimal location 57 on the enhance image 55 such that an alternative location may be outputted with module 140.

Optionally processing module 130 may provide and display to a user, a medical practitioner and/or nurse, on display 135 a plurality of optional optimal locations 57 about enhanced image 55. Preferably a user may select at least one or more optimal locations 57 via display 135 and/or a user interface.

Optionally a user, for example a medical practitioner and/or nurse, may define at least one or more optimal location 57 within enhanced image 55 that are displayed on display 135 that may be printed with output module 140.

Figure 3A:
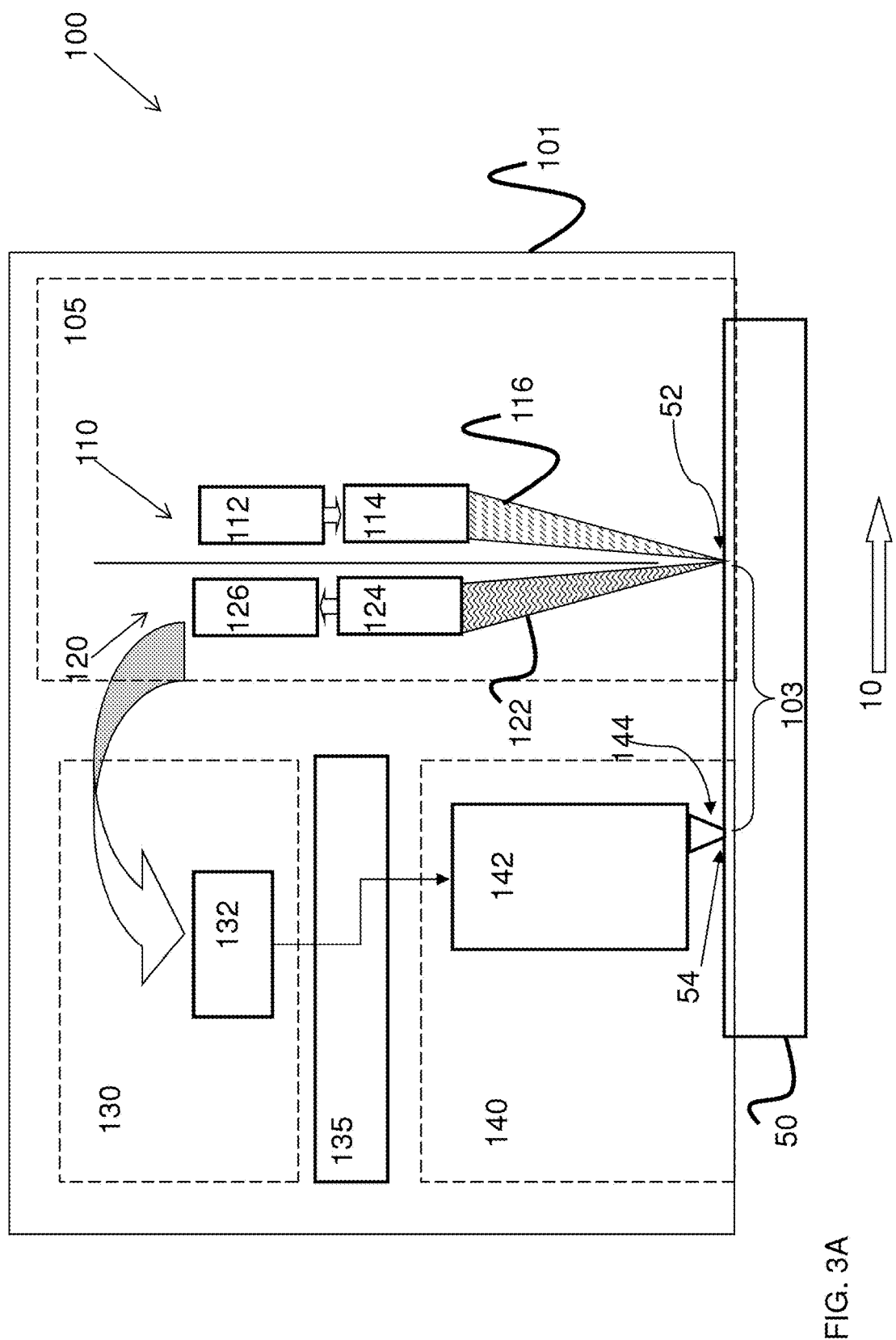
FIGS. 3A-D are schematic block diagrams of a system according to an optional embodiment of the present invention.
Figure 3B:
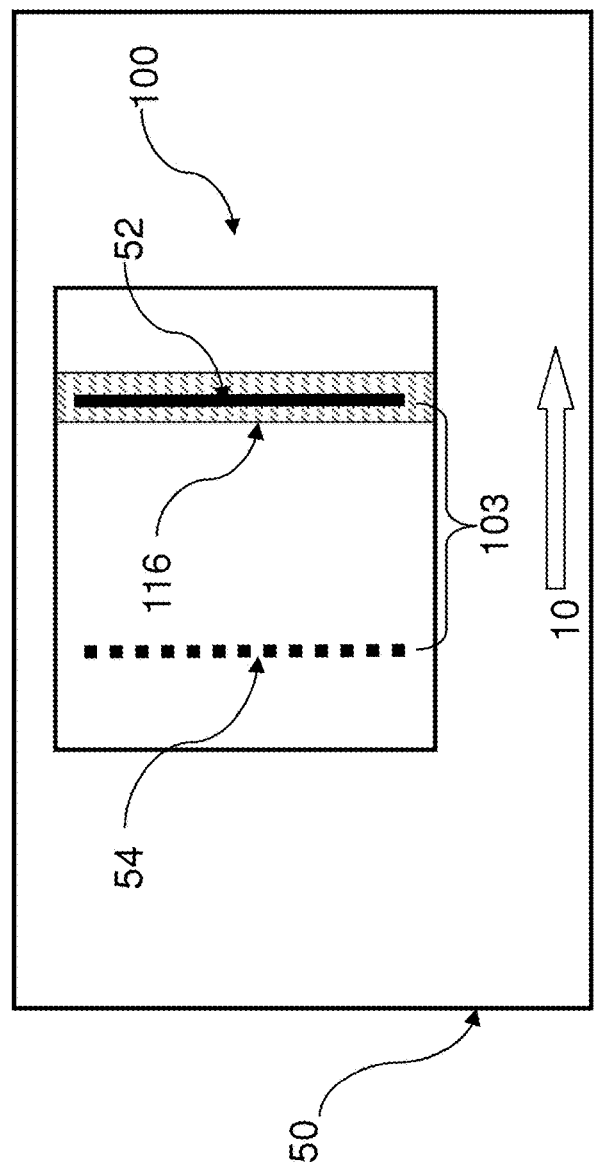
Figure 3C:
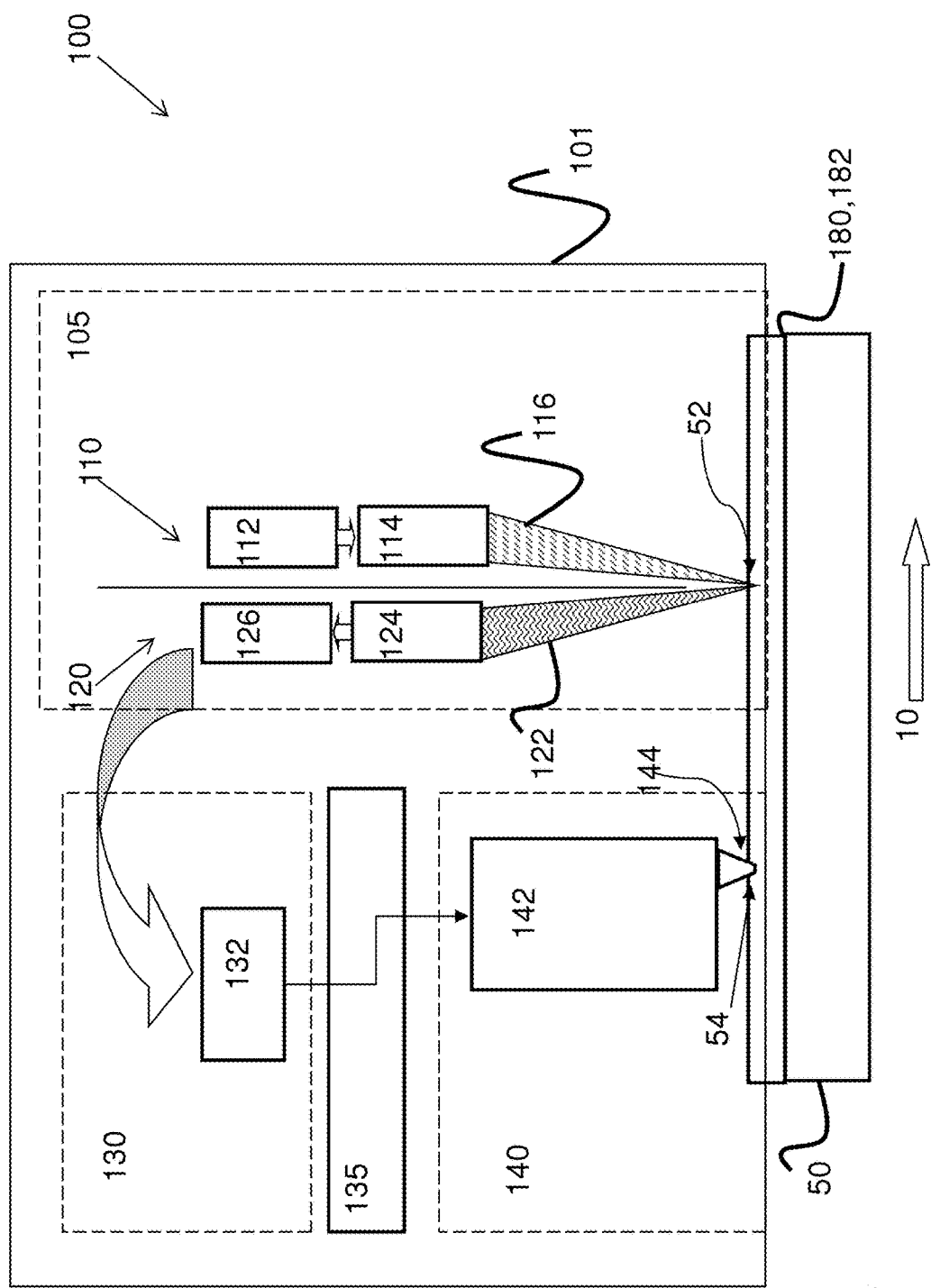
Figure 3D:
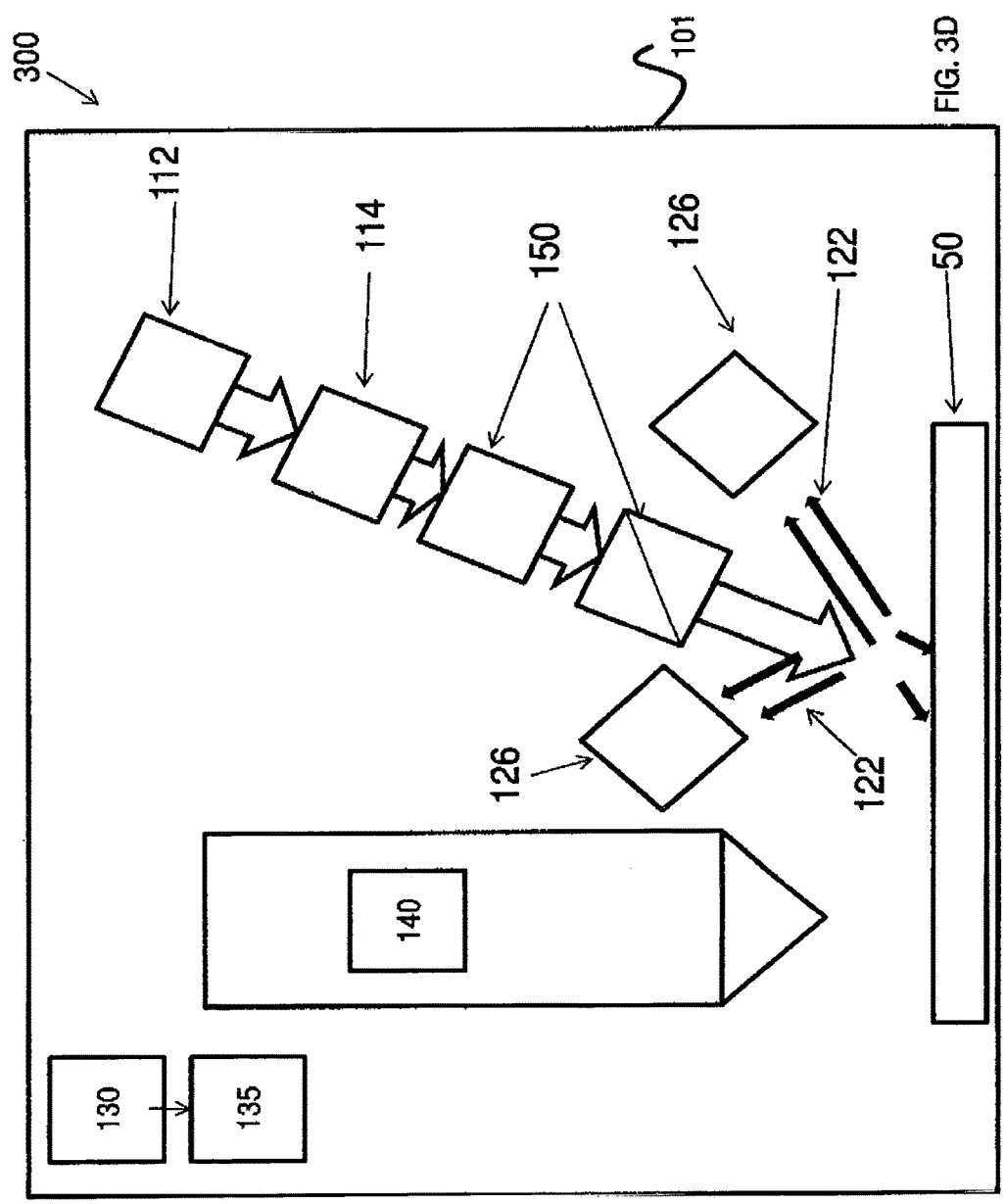

FIG. 3D shows an optional embodiment of system 100 embodied in system 300 similar to that described in FIGS. 3A and 3C, however further featuring optional enhancers 150 with the system 100 according to an optional embodiment. Most preferably optic enhancers 150 may be provided in the form of liquid crystal cell ('LCC') for example including but not limited to pi-cell liquid crystal, Twisted Nematic ('TN') liquid crystal cell, liquid crystal polarization rotator, liquid crystal polarization retarder, the like or any combination thereof.

FIG. 3D further shows system 100 comprising processor module 130 and display module 135 and further comprising an optional output module 140 provided in the form of a projector. Optionally a projector, for example a RG laser projector, may be utilized to project the enhanced image 55 (not shown) onto the target area 50.

Figure 2:
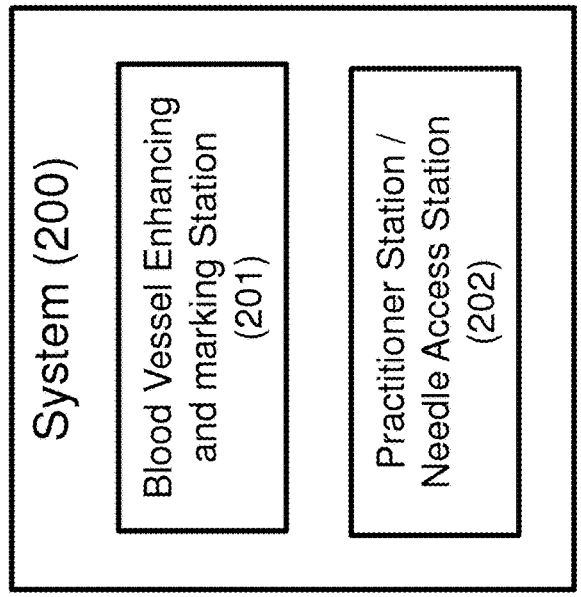
FIG. 2 is a schematic block diagram of an optional system set up according to an optional embodiment of the present invention.

FIG. 2 shows an optional embodiment of the present invention depicting system 200, optionally and preferably suited for situations where en-mass access to blood vessels is required, for example a laboratory setting. Most preferably system 200 comprises a blood vessel imaging station 201 and a practitioner station 202. Optionally system 200 may be realized in a laboratory setting where a large number of individuals require orderly access to blood vessel, for example for routine blood tests. In such a setting many individuals may first gain access imaging station 201 for identifying the blood vessel within a target area and thereafter approach a practitioner's station 202 for performing the blood test according the output of the imaging station 201. Therein an orderly system for example in a laboratory setting is provided to allow for en-mass access to single blood vessel enhancing system 100 may be provided for many individuals. Optionally a similar setting may be utilized in any en-mass situations for example hospital setting as part of the emergency room admittance process.

Most preferably system 200 may be realized where imaging station 201 comprises a blood vessel enhancing system 100 according to an optional embodiment of the present invention where most preferably housing 101 may be realized and/or configured to receive a particular target area for example the forearm, therein most preferably providing for en-mass automatic or semi-automatic use. Most preferably, housing 101 realized as an imaging station, allows system 100 to operate about the target area 10, for example the forearm, automatically or semi-automatically, such that a user gains access to the housing, system 100 performs the enhancing procedure and an output is provided about the target area, allowing the user (patient) to move onto the practitioner station 202. Most preferably system 200 provides for minimizing the use or need for trained and/or individuals specifically trained to use system 100.

Optionally and preferably, housing 101 may be configured with additional sanitization means to ensure proper sanitization prior to and following each use of sub-system 201. Optionally sanitization may be performed manually by a user, trained individual, and/or patient, more preferably sanitization may be performed automatically and/or semi-automatically.

FIG. 3A shows an illustrative depiction of system 100 having imaging module 105 comprising an illuminator module 110 and detector module 120. Most preferably illuminator module 110 comprises illumination source and/or generator 112 for producing the light source, that may be passed through at least one or more optical element 114 to produce an incident light beam 116 provided to illuminate target area 50. The illumination unit 110 preferably generates a line pattern and/or beam of light 116 that is projected onto target area 50, specifically at imaging line 52.

Most preferably light detector unit 120 may comprise detection units 122, 124, 126 provided for detecting reflected light 122 from target area 50 and converting it to an image of the target area most preferably for identifying any underlying blood vessels 55. Most preferably reflected light 122 may then be detected with detector 126 after passing through at least one or more optical element 124.

The illumination line 116 is generated from the light source 112 through optical element(s) 114. The light source 112 may be any kind of light source that has different optical properties such as absorption, scattering and reflection when interacting with a given target area 50 for example skin and blood vessel. Optionally an illumination source 112 may be provided in optional forms for example including but not limited to LEDs, Laser diodes and VCSELs, the like or any combination thereof.

Most preferably the illumination unit 110 and light source 112 may be controlled and/or driven with controller module 130 comprising a processor 132. Optionally control of the power supply and other operational parameters for example including but not limited to current, voltage, illumination unit 110 may be operated in optional formats for example including but not limited to continuous wave, pulsed or modulated mode, for example.

Optionally the light source 112 may be provided in the form of a light source having high polarization ratio and narrow band wavelength such as Laser diodes and VCSELs or LED with a polarizer. The high coherency of laser diodes and VCSEL increases the phenomena of speckles. To minimize the speckles contrast that cause for reduce of performance the light source can be driven in modulation mode. Additional technique to reduce speckle contrast is by the use of vibrating or rotating diffuser. The radiating light from the light source is shaped to a form of a rectangular illumination line 52 (hereinafter referred to as i-line) by optical element(s). The i-line beam 52 shaping optical elements are very common in the optics industry. One methods to generate the i-line is done by diffractive optical elements, this method is commonly used in scanning technology where the use diffractive waveguide that generate a line of uniform spots. One case where the line generator optics is not required is where the light source is in a form of a line shaped source generated by array of light emitters, for example 1×N LED source or 1×N array of VCSEL emitters. The illumination light might include in its path polarization optics (polarizer) and/or filters to optimize the results of blood vessel detection.

The reflected light 122, is a result of the reflection of incident light 116 after hitting the surface of target area 50. Reflected light 122 is collected by detection unit 126, most preferably comprising an array of sensors, most preferably light sensitive sensors. Optionally and preferably the light sensitive sensors forming detector 126 may for example include but is not limited to photodetectors, CCD, line CCD, CMOS, any combination thereof or the like. Optionally and preferably at least one or more light detectors may be utilized in detectors 126. Optionally and preferably two or more light detectors may comprise detector 126. Optionally a plurality of light detectors may provide a plurality of images that may be processed with processing module 130, optionally providing a plurality of layers that may be super imposed to further provide an improved and or enhanced image where the signal to noise ratio ('SNR') is improved therein further enhancing the image of the target area.

Reflected light 122 collection may optionally and preferably be optimized by using optics member 124, before light 122 is allowed to interact with sensors 126. Optionally optics member 124 may for example include a polarization optics, polarizer, filters, the like or any combination thereof to optimize the results blood vessel detection process.

Most preferably optics members 114, 124 may be provided in the form of a liquid crystal cell for example including but not limited to pi-cell liquid crystal, Twisted Nematic (TN) liquid crystal cell, liquid crystal polarization rotator, liquid crystal polarization retarder, the like or any combination thereof.

Optionally control of optics member 124 and its optical properties may be controlled with processing module 130. For example, reflected light 122 may be manipulated with a liquid crystal cell to rotate the polarity of light 122, where most preferably the degree of the rotation may be controlled with a control signal from a processor and/or controller, for example a control signal in the form of an electrical current. Optionally and preferably control of optics member 124 may be provided with respect to a plurality of optional parameters or system members, for example including but not limited to, the target area 50, image processing techniques utilized, type of illumination source 112, illumination unit 110, other optical members utilized 114, sensor 126, ambient environmental factors, type of filters or the like.

Most preferably, the collected signals retrieved by sensors 122 are processed with processing module 130, comprising a controller and/or microprocessor 132. Preferably module 130 provides for processing the signals and images, most preferably to generate a clear image of a blood vessel within target area 50.

Optionally and preferably processing module 130 provides for compensating for any mismatching and/or misalignment between the illumination unit 110 an detector unit 120.

Optionally and most preferably processing module 130 may further provide for identifying and/or locating an optimal needle access point within target area 50.

Most preferably a two dimensional image of a blood vessel within target area 50 may be obtained by the relative motion between the imaging system 100 and the target area 50, the direction shown with arrow 10.

Most preferably printing module 140 comprising a printer housing and electronics 142, printer head 144 and an ink reservoir (not shown). Optionally printing module 140 may be realized in the form of a plotter that provides for printing an image directly on the target area 50. Optionally a plotter may mark the target area with a line to represent the location of the underlying blood vessel based on the enhanced image provided by processing module 130. Optionally, the printer output may be provided in optional forms for example including but not limited to a tracing the outline of the blood vessel. Optionally the printer output may represent the external limits of the blood vessel, or may show the midline of the blood vessel. Optionally the blood vessel tracing may be provided in the form of a line drawing where the line properties may be solid line, dashed, continues, dotted or any line configuration indicative of the location. Optionally the printing may be provided using monochromatic ink, color ink, black ink, red ink, the like, any combination thereof, or any suitable marker or the like.

Optionally the printer may print directly on target area the optimal location 57 within the target area to gain access to the blood vessel. Optionally the optimal location may be identified with a specialized mark for example a circle, dot image, any geometric shape, the like or any combination thereof to indicate a preferred access point location. Optionally and preferably if the optimal location is identified and printed it may be printed alone without displaying the full blood vessel tracing. Optionally the optimal location may be identified with the blood vessel tracing for example as a background image.

Most preferably system 100 is configured such that scanning and printing may be performed substantially simultaneously following an initial delay period. Most preferably scanning is performed at scanning site 52 while printing is performed at a printing site 54. Optionally and preferably the distance between printing site and scanning site is configurable and may be proportional to at least one or more scanning parameters for example including but not limited to the scanning speed, shown by arrow 10, scanning distance 103 defined between scanning site 52 and printing site 54.

Most preferably the scanning distance 103 defined between the i-line 52 (scanning site) and the printing line 54 allots for the printing head 144 to paint the blood vessel data onto the target site 50 without obscuring the imaging optics.

Optionally the delay between the image capture with image capture module 105 of certain target area 52 to the printing time allots for the computer processing module 130 to process the captured image with processor 132 and to prepare the image for printing back onto the target area 50.

Optionally process 132 may communicate the captured and/or enhanced image to display 135 allowing a user, for example a medical practitioner and/or nurse, to visualize the enhanced image prior to outputting the image with output module 140. Optionally a user may interface with the enhanced image 55 where the user may select an optimal penetration point 57.

For example, scanning a distance 103 of about 3 cm and the relative scanning speed, depicted by arrow 10, is about 0.3 m/sec, configures a processing delay between the imaging and printing of about 0.1 sec. Most preferably a delay enables sufficient time for image processing to allow enhancement and optimization of the captured image by module 130 most preferably to generate good quality image for printing with printing module 150 about said target site.

Preferably, the scanning direction is not limited to a single axes, most preferably the printing line following the illumination line 52 and imagine lines 54.

Optionally printer head 144 may be utilized to convey the enhanced image of the blood vessel onto a target area 50. Optionally the target area 50 may be provided in optional forms for example including but not limited to the patient's skin, a substrate coupled to the patient's skin, a medium, skin, a biofilm, a biofilm the like or any combination thereof.

Optionally printer module 140 may optionally be provided can be an inkjet printer or relief printer. The image may be generated by a mechanical element for example including but not limited to a printer head, brush, India ink pen, the like or any combination thereof.

Optionally and most preferably the printer head is configured not to damage the target area. For example if printing directly on skin the printer head is configured not to damage the skin by applying the correct pressure. Optionally the printer head may be operated relative to a pressure threshold so as to ensure that the skin in not damaged. For example, the pressure applied by the printer head 144 to the target area 50 is most preferably configured to be lower than a damage threshold defined for the given target area 50 for example skin, and/or a substrate or the like.

Optionally, printer module 140 may utilized an ink that is most preferably biocompatible to allow contact with the skin.

FIG. 3B depicts a cut away bottom-up view, showing a partial view of system 100 from the perspective of target area 50. Target area 50 reveals both the imaging line, scanning site 52 parallel with printing line and/or site 54 separated by a scanning distance 103. Optionally and preferably printer head 144 is characterized in that incident line 116 may have a width area that may be larger than the width area of scanning site 52, for example as shown.

Most preferably the relationship between the size and/or shape of the incident beam 116 on target area 50 relative to the actual scanning line site 52 provides for reducing the requirement for perfect alignment between the illumination unit 110 and detectors unit 120. Optionally the ratio between scanning line 52 and illumination line 116 may be controlled relative to at least one or more parameters, for example including but not limited to: light source, type of incident light, wavelength, the polarity, type of target area, target area surface, the like or any combination thereof.

FIG. 3C shows an illustrative depiction of system 100 as shown in FIG. 3A however further showing a substrate 180 that interfaces system housing 101 and target area 50. Optionally substrate 180 may be provided in optional forms for example including but not limited to a gel, spray, fluid, foam, film, sticker, and/or sticker having a layer of analgesics, the like or any combination thereof. Most preferably image 55 may be printed onto medium 180, 182 with output module 140. Optionally medium 180, 182 may be provided in the form of a sticker 182 that is associated over target area 50. Optionally sticker 182 may be associated over target area 50 either before imaging area 50 or after imaging area 50.

Optionally sticker 182 may be provided in optional forms including a target (concentric circles) like sticker for example as shown in FIG. 4E, where the innermost circle identifies the optimal location 57 for needle penetration. Optionally output module 140 may provide for placing sticker 182 at the optimal location 57, for example without printing the full image 55.

Optionally and preferably sticker 182 is associated over target area prior to scanning target area 50, where output module 140 is allowed to print directly onto sticker 182 to output the optimal location 57 and or enhanced image 55 directly onto sticker 182.

Optionally sticker 182 and/or medium 180 may be associated over target area 50 after scanning with system 100. System 100 may be utilized to produce a printed output in the form of a sticker 182 having an image 55 already printed onto it and thereafter sticker 182 may be associated over target area 50. Optionally a target area 50 may be marked and/or a reference point may be placed over target area 50 so as to allow proper alignment of the printed sticker 182 over the target area 50. Most preferably the reference point may be printed on sticker 182 so as to ensure proper alignment between the reference points.

In FIG. 4A-D shows a schematic illustration of an output of the blood vessel enhancing system 100. FIG. 4A shows an optional output of system 100 comprising a printout of a detected blood vessel 55 within target area 50 where blood vessel 55 is printed and fully reproduced. FIG. 4B shows a further schematic illustration of an optional output printout of system 100 wherein the printout represents the midline of a potential blood vessel 55. Optionally, full color reproduction or an outlined image of blood vessel 55 printout may be provided for example as shown in FIGS. 4C and 4D.

FIG. 4F shows a further optional output according to the present invention where an optimal location 57 for needle point access about a target area 50 may be identified by system 100 as an output. Optionally and preferably identification of optimal location 57 may be provided by processing module 130 for example by image processing. Optionally identification of optimal location may be provided by considering a plurality of parameters for example including but not limited to vessel size, vessel thickness, vessel length, vessel surrounding tissue, tissue type, target area, V-noise, patient preferences, target area surface, tattoos, landmarks, the like, or any combination thereof. Optionally optimal location 57 may be marked and/or identified in a plurality of optional formats for example including but not limited to an image printout directly on the surface of the target area 50, a marking, stamping, coupling a sticker about the optimal location 57, the like or any combination thereof.

FIG. 4E shows an optional output of system 100 provided substrate 180 in the form of a sticker 182 that is placed over optimal location 57 within target area 50. As shown, sticker 182 may comprise concentric circles wherein the innermost circle defines the optimal needle access point and the optimal target location 57. Optionally and preferably the innermost circle may be peeled to allow direct access to target location 57.

Optionally sticker 182 may further comprise a portion 184 for communicating and/or conveying a textual message such as +'ve HIV status, +'ve Hep-C status, blood type, time and date stamp of scan, the like or any combination thereof.

Optionally optimal location 57 may be marked with output module 140, for example by way of placing a sticker or the like substrate onto the optimal location within the target area 50, for example as shown in FIG. 7E. Optionally and preferably sticker and/or substrate identifying location 57 may be provided with a recess and/or opening providing a needle access point. Optionally a sticker 182 and/or substrate may be provided in a storage cartridge, 142, associated with output module 140 that provides for places the sticker about the optimal location 57, for example as may be provided by a plotter or the like type printer according to the appropriate coordinates with target area 50 identifying optimal location 57.

Optionally the printing pattern utilized may be provided according to user preferences for example a practitioner, nurse or physician. Optionally printing pattern may be decorative to sooth kids and/or infants.

Optionally substrate 180 and/or sticker 182 may be provided in the form of an analgesic patch and/or comprise a layer comprising analgesics to alleviate any pain. Optionally the analgesic may be released once the sticker and/or analgesic layer is removed prior to administration of the needle.

Optionally the detected blood vessel 55 may be printed as a line on the skin surface of target area 50 therein on top of the blood vessel where optionally the line thickness may be equal to that thickness of blood vessel 55, optionally the line may be solid and/or dotted and/or broken.

Optionally detected blood vessel 55 may be printed in optional color and/or utilize a color scheme for conveying the quality of an underlying blood vessel, for example based on the thickness of the blood vessel. For example, a red line may be utilized for good and/or preferable and/or thick blood vessel while a blue line may be utilized to indicate a less preferably and/or small and/or thin blood vessel. Optionally the line may be solid and/or dotted and/or broken.

Optionally the ink utilized to print the image of a detected blood vessel 55 may be biocompatible and/or inter ink.

Optionally the printing patters may utilized printout lines that may be solid and more preferably dotted line and/or broken line. Most preferably dotted and/or broken line pattern printing provides space in the broken line portion to allow sufficient space for a needle to penetrate the skin without risking un-necessary exposure to the ink.

Optionally the ink utilized may be such that requires exposure with a secondary substrate in order to reveal it, and/or is only revealed under certain conditions and/or is activated with an external device. For example, the ink utilized may be such that is only revealed to the naked eye when exposed to specific light and/or substrate for example UV light ink that is exposed under UV light. Optionally the ink and image may be viewed only following exposure to a secondary substrate and/or with an auxiliary device capable of revealing the ink pattern.

Optionally, a dual ink patterns may be provided utilizing both visible ink, visible to the naked eye, as well as non-visible ink not readily visible to the naked eye. Optionally such dual ink provides for printing a child-friendly patterns such as tattoos and/or cartoons characters or the like figures and/or picture may be printed with visible ink while the blood vessel image 55 may be printed in non-visible ink and revealed to a practitioner under exposing conditions, for example UV and/or infrared light and/or with a suitable accessory device. Optionally such dual ink utilization provides for facilitating the blood extraction by a practitioner's, particularly suitable for children.

FIG. 5 shows an optional embodiment of the present invention depicting a portion of system 200 as described in FIG. 2, specifically showing the blood vessel enhancing system 100 wherein housing 101 is realized as blood vessel enhancing and identification station 201, as previously described.

As previously described, system 200 comprises a blood vessel imaging station 201 and a practitioner station 202 (not shown). Optionally system 200 may be realized in a laboratory setting where a large number of individuals require orderly access to blood vessel, for example for routine blood tests. In such a setting many individuals may first gain access to imaging station 201 for identifying the blood vessel within a target area and thereafter approach a practitioner's station 202 for performing the blood test according to the output of the imaging station 201. Therein an orderly system laboratory setting is provided to allow for en-mass access to single device for many individuals. Optionally a similar setting may be utilized in any en-mass situations for example hospital setting as part of the emergency room admittance process.

FIG. 5 shows a schematic illustrative blood vessel enhancing system 100 where housing 101 is realized as part of an imaging station. Most preferably housing 101 is configured to receive a particular target area 50 for example as shown in the form of forearm 15. Optionally housing 101 may be configured to receive any target area about a patient's anatomy.

Most preferably housing 101 is adapted and/or confirmed to receive and/or associate with forearm 15, for example as shown housing 18, having a recess and/or two housing members, for example as shown. Most preferably a patient associates forearm 15 with housing 18 to allow system 100 to perform the imaging and output process, according to optional embodiment of the present invention.

Optionally housing 18 may be configured to be stationary housing or mobile housing relative to the target area 50. Optionally housing 18 may be configured to be mobile, for example about a track and/or railing system, while the functional portions of system 100 are configured to be stationary about target area 50.

Most preferably housing 18 is configured to be stationary while the functional portion of system 100 are configured to be mobile about target area 50, for example as shown. For example, housing 18 may comprise a recess and or rail 22 that provides for sliding the blood vessel enhancer system 100 comprising illumination head 19, imaging line 20 and output head 21, along the length of rail 22, most preferably to capture and enhance image of the underlying blood vessel with a processing module (not shown). The movement of the system 100 about rail 22 may optionally be executed manually by an operator and/or user and/patient. More preferably movement of system 100 about rail 22 may be provided semi-automatically, and most preferably automatically, for example by utilizing actuators and/or motors (not shown).

As shown, system 100 advanced about forearm 15 in the direction depicted by arrow 10, therein showing the output 17 of system 100 in previously scanned as well as of yet un-scanned area 16 about forearm 15 where the blood vessel is not revealed.

Figure 6:
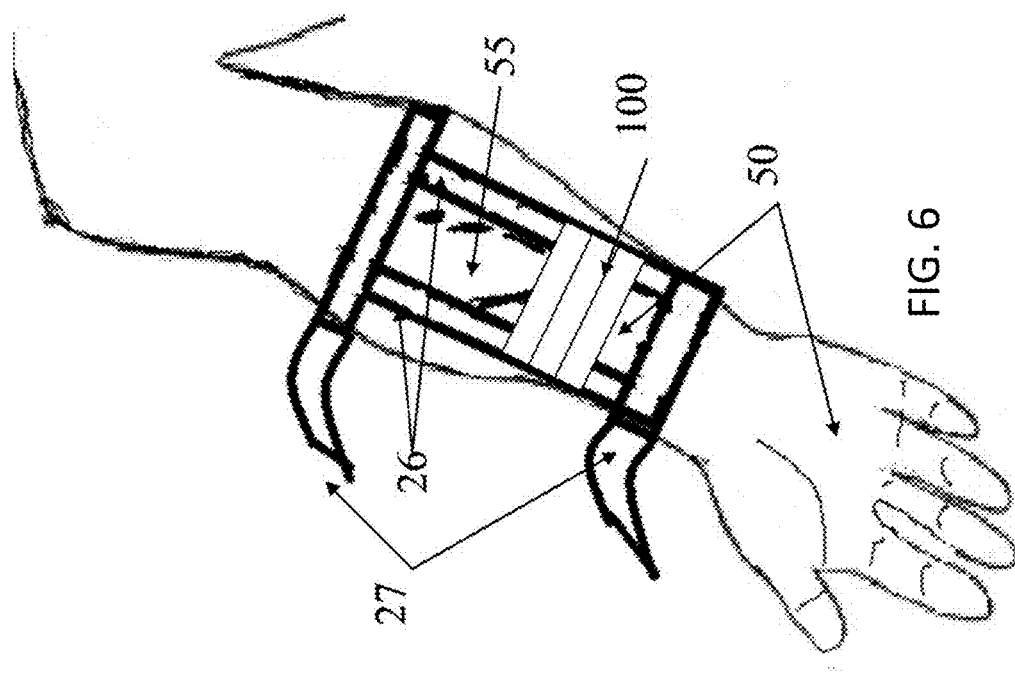
FIG. 6 shows a schematic illustration of an optional embodiment of the present invention.

FIG. 6 shows a further optional embodiment of the present invention for system 100 where an auxiliary fixation device 27 may be associated or otherwise coupled system 100 about housing 101. Most preferably auxiliary device 27 may provide for associating system 100 about a target area 50, for example the forearm as shown. Optionally and preferably auxiliary device 27 may comprise railing and/or track system 26 to associate with device 100 and to maneuver system 100 about its length, to produce an enhanced image of underlying detected blood vessel 57 that is identified with system 100.

Optionally auxiliary device 27 and rail 26 may be integrated with housing 101, so as to form a mobile system 100, that may optionally be realized as a handheld device.

Optionally housing 101 may be configured to shield ambient light to improve the performance of system 100.

Optionally housing 101 may be fit with mechanical mobility features to facilitate motility of system 100 about target area 50, for example including but not limited to wheels, frictionless rollers, frictionless ball bearings, sliders, the like or any combination thereof. For example housing 101, depicted in FIGS. 5 and 6, may comprise wheels and/or rollers for sliding the system 100 about target area 50 over the respective rails as shown. Optionally and preferably such wheels may provide for reducing and/or avoiding friction between portions of system 100 and the target area 50. Optionally moving the system 100 over the target area 50 with wheels may stretch target area 50 providing better scanning and printing performance.

Figure 7:
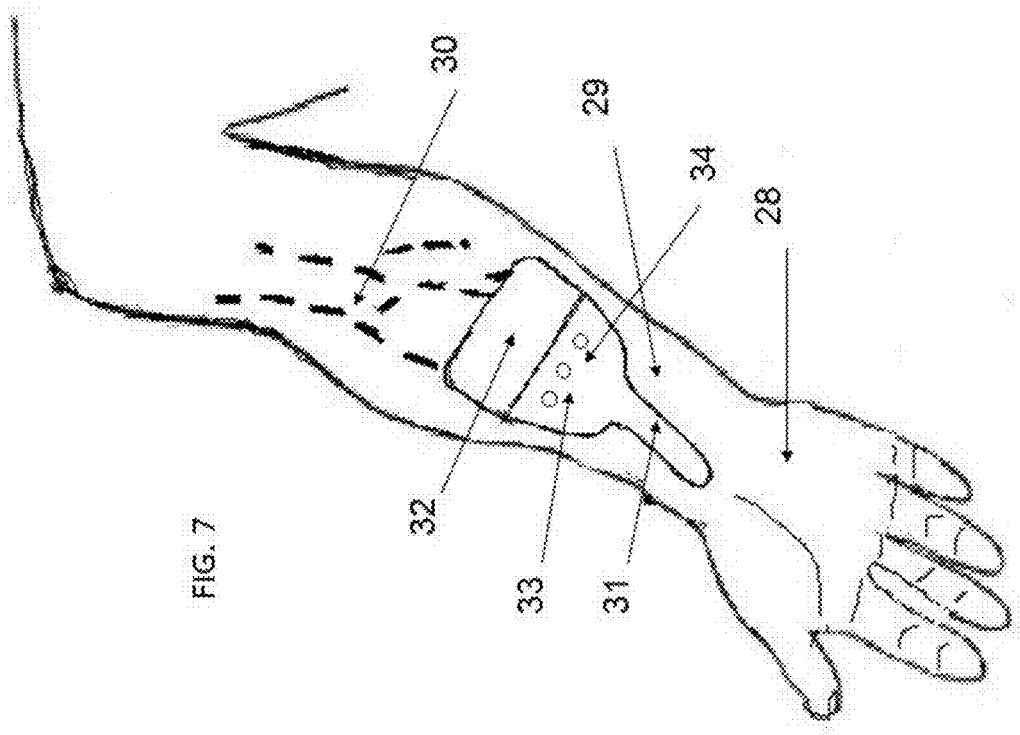
FIG. 7 shows a schematic illustration of an optional embodiment of the present invention, showing an optional hand held mobile depiction of the system according to an optional embodiment of the present invention.

FIG. 7 depicts a further optional embodiment of the system 100 depicted in the form of stand-alone unit, mobile hand-held unit, most preferably depicted by a specialized configuration of housing 101. Most preferably housing 101 comprises a handle 31 and the scanning and printing head 32. Processing module 130 may comprise a user interface and/or display for example in the form of indicators 33 and/or buttons 34 to facilitate operation of system 100 while providing user information.

As shown, the target areas comprises two parts of the arm 28 are shown, the area 30 that was scanned by the system 100 where the detected blood vessels are marked, and the portion of the target area 29 that has not been scanned with system 100.

Optionally, housing 101 may be configured to be shielded and/or opaque to ambient light to provide better performance.

FIG. 8 shows a flowchart of an optional method of use of system 100 according to the present invention. First in stage 800, system 100, most preferably housing 101 is coupled over target area 50. An optional embodiment utilizing a substrate 180 for example a sticker 182 onto which the enhanced blood vessel image 55 and/or the optimal location 57 is printed and/or outputted and/or displayed may require optional stage 800s wherein the output medium 180, for example a sticker 182, is associated over the target area 50 prior to obtaining the image of the target area. Optionally during stage 800 a practitioner may mark and define target area 50 and/or mark a reference point within the target area 50. Optionally and preferably the reference point may be utilized to facilitate alignment between a printout of system 100 and the scanned target area, for example as described in FIG. 3C-D.

Next in stage 801 an image of target area 50 is obtained with system 100, as previously described. Optionally the method of obtaining the image may be provided by way of scanning the target area or by way of imaging the entire target area 50 with a static image. Optionally imaging target area 50 may be provided with at least one or more or a plurality of light sensors and/or detectors 126, as previously described.

Next in stage 802, image processing of the image of the target area 50 is performed most preferably by processing module 130. Most preferably image processing provides for producing an enhanced image of a blood vessel 55 detected within the target area 50.

Optionally following detection of blood vessel 55 the image may be displayed on display 135 and/or may be outputted to output module 140. Optionally display 135 allows a practitioner to interface with the enhanced image 55 prior to printing and/or outputting it with module 140. Optionally display 135 allows a user the opportunity to select and/or determine at least one optimal location 57 along enhance image 55.

Preferably output module 140 allows a practitioner to visualize the detected blood vessel 55 and/or the optimal access point location 57 about vessel 55 directly on target area 50.

Next in stage 803 the enhanced image identifying the blood 55 vessel underlying the target area 50 is outputted with output module 140. Most preferably the image 55 and/or target 57 is outputted onto a medium 180, 182 for example by way of printing with a printer head, as previously described.

Optionally output module 140 may mark an area for optimal needle penetration 57 utilizing a substrate 180 for example sticker 182 or the like external marker.

Optionally output module 140 may produce a printout onto a substrate 180 more preferably a sticker 182, the printout including an image of the enhanced image 55 and a reference point, where the sticker 182 is then associated over the target area 50 having a corresponding reference (stage 800) using the corresponding reference point to align the sticker.

Optionally image 55 and/or target may be directly printed and or marked onto the target area 50. Optionally and preferably output image 55 may be printed and/or outputted onto a medium and/or substrate, for example a sticker, that may be associated with target area 50 and/or system 100 at the same time as output module 140 prints the image 55. Optionally output module 140 may print the image 55 onto a sticker that was previously associated over target area 50, as provided in optional stage 800$s$.

Optionally optional stage 804 may be performed next wherein, the image 55, 57 outputted in stage 803 may be revealed, for example by a secondary process or by utilizing an auxiliary device 160. Optionally if image 55, 57 is outputted onto a medium and/or substrate it may be revealed in optional stage 804. Optionally revealing image 55,57 may require exposure to an exposing substance for example including but not limited to water, alcohol, a chemical substrate, fluid, paint, film, light, light at a particular wavelength, heat, exposure to temperature change, the like or any combination thereof.

Finally once image 55,57 is revealed a practitioner, for example a nurse or physician, may visualize the location of the detected blood vessel 55 and/or optimal access point location 57 underlying the target area 50, prior to undertaking needle access to the blood vessel.

In another embodiment of the current invention a disposable transparent spacer may be used to separate between imaging device and the skin such that the space may be replaced for every new patient, preferably to reduce the risk of any contamination between patients. The transparent spacer may have an option to open the location for the printing head, so it can print the skin through that opening.

Other option is to print the full image on the spacer and to expose the desired location for needle insertion by peeling off a part of the printed spacer.

There are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

Importantly, this Summary may not be reflective of or correlate to the inventions protected by the claims in this or continuation/divisional applications hereof. Even where this Summary is reflective of or correlates to the inventions protected by the claims hereof, this Summary may not be exhaustive of the scope of the present inventions.

While the invention has been described with respect to a limited number of embodiment, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

Further modifications of the invention will also occur to persons skilled in the art and all such are deemed to fall within the spirit and scope of the invention as defined by the appended claims.

While the invention has been described with respect to a limited number of embodiments, it will be appreciated that many variations, modifications and other applications of the invention may be made.

What is claimed is:

1. An optical blood vessel enhancing system for identify a blood vessel within a target area, the system comprising:
    a. a light source configured to transmit at least one wavelength incident light within the infrared spectrum onto said target area, said light source comprising at least one wavelength;
    b. an optical sensor responsive to said infrared spectrum light, wherein said optical sensor is configured to receive light reflected from said target area therein forming a contrasted image based on said reflected light and at least a selective portion of said incident light;
    c. a controllable optical enhancer in the form of a controllable polarizer provided for controlling the optical properties of at least one of said incident light and/or said reflected light; and
    d. a processor functionally coupled with said optical sensor for enhancing said contrasted image to identify a blood vessel with said target area by distinguishing between a potential blood vessel from the surroundings target area; and for controlling said controllable optical enhancer; wherein enhancing said contrasted image is provided for with said processor and includes:
        i) obtaining a plurality of images of the target area, characterized in that each image is obtained at a different polarity rotation; and
        ii) said plurality of images are evaluated relative to one another by way of superimposing said plurality of images to define said enhanced image.

2. The blood vessel enhancing system of claim 1 comprising at least two controllable optical enhancers wherein each of said optical enhancer is a polarizer;
    a first controllable optical enhancer disposed about said light source for controlling the optical properties of said incident light;

a second controllable optical enhancer disposed about said optical sensor for controlling the optical properties of said detected reflected light;

and wherein said optical processor provides for controlling said first optical enhancer and said second optical enhancer with respect to one another.

3. The blood vessel enhancing system of claim 2 wherein said polarizers are selected from S rotation polarizer or P rotation polarizer.

4. The blood vessel enhancing system of claim 2 further comprising at least two polarizers disposed about said optical sensor and at least two polarizers disposed about said light source.

5. The blood vessel enhancing system of claim 1 wherein said optical enhancer is provided in the form selected from: a motorized rotating polarizer, a liquid crystal cell (LCD), pi-cell liquid crystal, TN (twisted nematic) liquid crystal cell, liquid crystal polarization rotator, liquid crystal polarization retarder, and any combination thereof.

6. The blood vessel enhancing system of claim 1 further comprising:
   a. a printer to mark the blood vessel within said target area to reveal the blood vessel locations therein; and
   b. a fixation module to minimize or prevent relative movement between the imaging module and the printer head to ensure that the blood vessel will be marked at correct locations.

7. The blood vessel enhancing system according to claim 6 wherein said printer comprises a printer head to print on the skin surface a visual pattern of the blood vessel.

8. The blood vessel enhancing system according to claim 7 wherein said visual pattern is formed from a biocompatible ink that marks the blood vessel on the skin surface.

9. The blood vessel enhancing system according to claim 7 comprises an ink that can be seen only when exposed to UV or IR light with suitable accessory.

10. The blood vessel enhancing system according to claim 1 wherein said light source transmits light at a wavelength in the range of 455 nm to 940 nm.

11. The blood vessel enhancing system according to claim 1 further comprising a display screen for displaying.

12. The blood vessel enhancing system according to claim 11 wherein the display screen comprises controls to permit selection of a needle insertion site on-said contrasted image being transmitted thereon.

13. The blood vessel enhancing system of claim 1 further comprising a housing configured in the form of as a hand-held mobile device.

14. The blood vessel enhancing system of claim 1 further comprising an output module configured to print said enhanced contrasted image onto a medium disposed about or coupled onto said target area.

15. The blood vessel enhancing system of claim 14 wherein said medium is selected from the group including at least one or more of:
   a) a sticker;
   b) a sticker provided in matrix form comprising a plurality of removable sticker segments;
   c) a light sensitive medium;
   d) a medium coated with a light sensitive material;
   e) a medium coated with a light sensitive film;
   f) a medium that is light sensitive to a particular wavelength;
   g) a medium that is light sensitive to a wavelength spectrum range;
   h) a sticker including an opening or recess defining the needle access point;
   i) a ring shaped sticker including an opening or recess defining a needle access point.

16. The blood vessel enhancing system claim 15 wherein said enhanced contrasted image may be revealed onto a medium by exposure to a secondary exposing material and wherein said secondary exposing material is selected from the group consisting of: alcohol, water, flowing fluid, gas, magnetic field, electromagnetic field, electrical current, paint, film, DC current, or any combination thereof.

17. A processor mediated method for enhancing an optical image of a blood vessel for identifying the blood vessel within a target area, the method comprising;
   a) obtaining a plurality of polarized images of a target area wherein each image is polarized at a different polarity rotation;
   b) selectively layering a group of at least two or more of said plurality of polarized images to form an enhanced image of the target area; and
   c) outputting the enhanced image to at least one selected from the group consisting of: an output module, printer, display, display module, projection apparatus.

18. The method of claim 17 wherein all of said plurality of polarized images are layered.

19. The method of claim 17 wherein said layering comprises superimposing at least two of more of said plurality of polarized images.

20. The method of claim 17 wherein the group of at least two or more of said plurality of polarized images selected to form said enhanced image is based on the resultant Signal to Noise Ratio ('SNR').

* * * * *